United States Patent
Mainfeld et al.

(10) Patent No.: US 10,584,100 B2
(45) Date of Patent: Mar. 10, 2020

(54) SOLID STATE FORMS OF NETARSUDIL MESYLATE

(71) Applicant: Assia Chemical Industries Ltd., Petach Tikva (IL)

(72) Inventors: Alexander Mainfeld, Petah-Tikva (IL); Sharona Shachan-tov, Kfar-Saba (IL); Ariel Mittelman, Elad (IL); Rotem Sella-Erez, Tel-Aviv (IL); Yifat Ronen, Ramat Gan (IL); Tamar Nidam, Yehud (IL)

(73) Assignee: ASSIA CHEMICAL INDUSTRIES LTD., Petach Tikva (IL)

( * ) Notice: Subject to any disclaimer, the term of this patent is extended or adjusted under 35 U.S.C. 154(b) by 0 days.

(21) Appl. No.: 16/559,829

(22) Filed: Sep. 4, 2019

(65) Prior Publication Data

US 2019/0389807 A1    Dec. 26, 2019

Related U.S. Application Data

(62) Division of application No. 15/886,024, filed on Feb. 1, 2018, now Pat. No. 10,442,770.

(60) Provisional application No. 62/469,214, filed on Mar. 9, 2017, provisional application No. 62/453,764, filed on Feb. 2, 2017.

(51) Int. Cl.
*C07D 217/22*    (2006.01)
*A61P 27/06*    (2006.01)

(52) U.S. Cl.
CPC ............ *C07D 217/22* (2013.01); *A61P 27/06* (2018.01); *C07B 2200/13* (2013.01)

(58) Field of Classification Search
CPC .......................... C07D 217/22; C07B 2200/13
See application file for complete search history.

(56) References Cited

U.S. PATENT DOCUMENTS

| | | | |
|---|---|---|---|
| 8,394,826 B2 | 3/2013 | Delong et al. | |
| 9,643,927 B1 | 5/2017 | Sturdivant et al. | |
| 10,442,770 B2 * | 10/2019 | Mainfeld | C07D 217/22 |
| 2018/0055833 A1 | 3/2018 | Lin et al. | |
| 2018/0215715 A1 | 8/2018 | Mainfeld et al. | |

FOREIGN PATENT DOCUMENTS

| | | |
|---|---|---|
| CN | 107434780 A | 12/2017 |
| WO | 2010126626 A2 | 11/2010 |
| WO | 2014144781 A1 | 9/2014 |

* cited by examiner

*Primary Examiner* — James D. Anderson
(74) *Attorney, Agent, or Firm* — Cantor Colburn LLP (57) ABSTRACT

Disclosed are solid state forms of Netarsudil mesylate, processes for preparation thereof, uses thereof, and pharmaceutical compositions thereof.

9 Claims, 7 Drawing Sheets

SOLID STATE FORMS OF NETARSUDIL MESYLATE

CROSS-REFERENCE TO RELATED APPLICATIONS

This application is a divisional of U.S. application Ser. No. 15/886,024, filed Feb. 1, 2018, which claims the benefit of U.S. Provisional Application Nos. 62/453,764 filed Feb. 2, 2017 and 62/469,214 filed Mar. 9, 2017, which are hereby incorporated by reference in their entirety.

FIELD OF THE INVENTION

The present invention relates to solid state forms of Netarsudil mesylate, processes for preparation thereof and pharmaceutical compositions thereof.

BACKGROUND OF THE INVENTION

Netarsudil, has the chemical name Benzoic acid, 2,4-dimethyl-, (4-((1S)-1-(aminomethyl)-2-(6-isoquinolinylamino)-2-oxoethyl)phenyl)methyl ester. Netarsudil has the following chemical structure:

Netarsudil ophthalmic solution (Rhopressa (R)) 0.02% was approved for the lowering of elevated intraocular pressure (IOP) in patients with open-angle glaucoma or ocular hypertension by the FDA.

Netarsudil and process for preparation thereof are known from WO2010/126626. In said process Netarsudil is separated from a racemic mixture by chiral chromatography or salt formation one step before the final API.

The dimesylate salt of Netarsudil is disclosed in WO2014/144781 and process for preparation thereof is disclosed in U.S. Pat. No. 9,643,927.

Polymorphism, the occurrence of different crystal forms, is a property of some molecules and molecular complexes. A single compound, like Netarsudil, may give rise to a variety of polymorphs having distinct crystal structures and physical properties like melting point, thermal behaviors (e.g. measured by thermogravimetric analysis—"TGA", or differential scanning calorimetry—"DSC"), powder X-ray diffraction (XRPD) pattern, infrared absorption fingerprint, Raman absorption fingerprint, and solid state ($^{13}C$-) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, improving the dissolution profile, or improving stability (polymorph as well as chemical stability) and shelf-life. These variations in the properties of different salts and solid state forms may also provide improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new salts, solid state forms and solvates of a pharmaceutical product can provide materials having desirable processing properties, such as ease of handling, ease of processing, storage stability, and ease of purification or as desirable intermediate crystal forms that facilitate conversion to other salts or polymorphic forms. New salts, polymorphic forms and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life. Accordingly, there is a need for solid state forms of Netarsudil and salts thereof.

SUMMARY OF THE INVENTION

The present disclosure relates to solid state forms of Netarsudil and salts thereof, in particular Netarsudil mesylate, to processes for preparation thereof, and to pharmaceutical compositions comprising these solid state forms.

The present disclosure also provides uses of the solid state forms of Netarsudil and salts thereof for preparing other solid state forms of Netarsudil, Netarsudil salts and solid state forms thereof.

In another embodiment, the present disclosure encompasses the above described solid state forms of Netarsudil and salts thereof for use in the preparation of pharmaceutical compositions and/or formulations, preferably for the treatment of glaucoma or ocular hypertension.

In another embodiment the present disclosure encompasses the use of the above described solid state form of Netarsudil and salts thereof for the preparation of pharmaceutical compositions and/or formulations comprising Netarsudil as a single API or in combination with other active ingredients.

The present disclosure further provides pharmaceutical compositions comprising the solid state forms of Netarsudil and salts thereof according to the present disclosure.

In yet another embodiment, the present disclosure encompasses pharmaceutical formulations comprising the above described solid state forms of Netarsudil and salts thereof and at least one pharmaceutically acceptable excipient, preferably for local treatment in a form of ophthalmic solution.

The present disclosure encompasses processes to prepare said pharmaceutical formulations of Netarsudil and salts thereof comprising combining the above solid state forms and at least one pharmaceutically acceptable excipient.

The solid state forms as defined herein, as well as the pharmaceutical compositions or formulations of the solid state form of Netarsudil and salts thereof, can be used as medicaments, particularly for the treatment of glaucoma or ocular hypertension.

The present disclosure also provides methods of treating glaucoma or ocular hypertension, comprising administering a therapeutically effective amount of Netarsudil and salts thereof of the present disclosure, or at least one of the above pharmaceutical compositions or formulations, to a subject suffering from glaucoma or ocular hypertension, or otherwise in need of the treatment.

The present disclosure also provides uses of the solid state forms of Netarsudil and salts thereof of the present disclosure, or at least one of the above pharmaceutical compositions or formulations for the manufacture of a medicament for treating glaucoma or ocular hypertension.

DETAILED DESCRIPTION OF THE INVENTION

The present disclosure relates to solid state forms of Netarsudil and salts thereof, in particular Netarsudil mesylate, processes for preparation thereof and pharmaceutical compositions comprising said solid state forms.

The solid state forms of Netarsudil and salts thereof according to the present disclosure may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents and advantageous processing and handling characteristics such as compressibility, or bulk density.

A crystal form may be referred to herein as being characterized by graphical data "as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Netarsudil and salts thereof referred to herein as being characterized by graphical data "as depicted in" a Figure will thus be understood to include any crystal forms of the Netarsudil and salts thereof, characterized with the graphical data having such small variations, as are well known to the skilled person, in comparison with the Figure.

A solid state form (or polymorph) may be referred to herein as polymorphically pure or substantially free of any other solid state (or polymorphic) forms. As used herein in this context, the expression "substantially free of any other forms" will be understood to mean that the solid state form contains about 20% or less, about 10% or less, about 5% or less, about 2% or less, about 1% or less, or about 0% of any other forms of the subject compound as measured, for example, by XRPD. Thus, solid state of Netarsudil and salts thereof, described herein as substantially free of any other solid state forms would be understood to contain greater than about 80% (w/w), greater than about 90% (w/w), greater than about 95% (w/w), greater than about 98% (w/w), greater than about 99% (w/w), or about 100% (w/w) of the subject solid state form of Netarsudil and salts thereof. Accordingly, in some embodiments of the disclosure, the described solid state forms of Netarsudil and salts thereof may contain from about 1% to about 20% (w/w), from about 5% to about 20% (w/w), or from about 5% to about 10% (w/w) of one or more other solid state forms of the same Netarsudil and salts thereof.

As used herein, unless stated otherwise, XRPD peaks reported herein are preferably measured using CuK α radiation, $\lambda=1.5418$ Å.

As used herein, the term "isolated" in reference to solid state forms of Netarsudil and salts thereof, of the present disclosure corresponds to solid state forms of Netarsudil and salts thereof that are physically separated from the reaction mixture in which it is formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C. A process or step may be referred to herein as being carried out "overnight." This refers to a time interval, e.g., for the process or step, that spans the time during the night, when that process or step may not be actively observed. This time interval is from about 8 to about 20 hours, or about 10 to about 18 hours, typically about 16 hours.

The term "solvate", as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

The crystal hydrate indicated by single crystal analysis or by water analysis by Karl Fischer (KF) titration or by TGA analysis of this product is believed to have been produced as a result of water introduced from the atmosphere in which this material was processed, or by traces of water present in the solvents that were in contact with the material, or a combination of these factors.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding methyl tert-butyl ether (MTBE) (1.5 v/v) to a 100 ml reaction mixture would indicate that 150 mL of MTBE was added.

As used herein, the term "reduced pressure" refers to a pressure of about 10 mbar to about 50 mbar.

As used herein, and unless stated otherwise, the term "anhydrous" in relation to crystalline Netarsudil and salts thereof relates to a crystalline Netarsudil and salts thereof which does not include any crystalline water (or other solvents) in a defined, stoichiometric amount within the crystal. Moreover, an "anhydrous" form does not contain more than 1% (w/w) of either water or organic solvents as measured for example by TGA.

The present disclosure comprises a crystalline form of Netarsudil mesylate designated as form N1. The crystalline form N1 of Netarsudil mesylate can be characterized by data selected from one or more of the following: a XRPD pattern having peaks at 5.8, 11.9, 17.8, 19.9 and 23.8 degrees 2-theta±0.2 degrees 2-theta; a XRPD pattern as depicted in FIG. 1; or combinations of these data.

Crystalline form N1 of Netarsudil mesylate may be further characterized by the XRPD pattern having peaks at 5.8, 11.9, 17.8, 19.9 and 23.8 degrees 2-theta±0.2 degrees 2-theta, and also having one, two, three or four additional peaks at 6.8, 21.2, 24.5 and 26.6 degrees 2-theta±0.2 degrees 2-theta; and combinations of these data.

Figure 1:
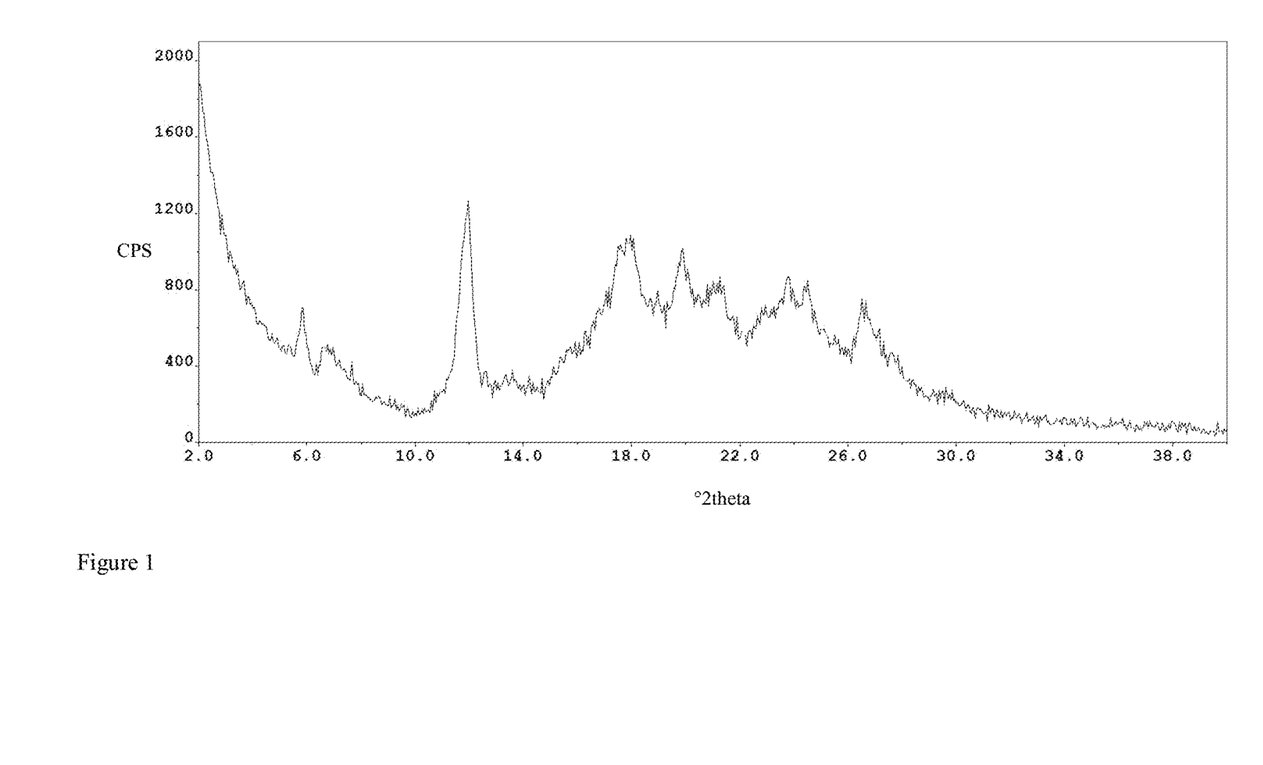
FIG. 1 shows a powder X-ray diffraction pattern ("powder XRD" or "XRPD") of Netarsudil mesylate form N1 obtained in Example 1.

Crystalline form N1 of Netarsudil mesylate may be characterized by each of the above characteristics alone/or by all possible combinations, e.g., by XRPD pattern having peaks at 5.8, 11.9, 17.8, 19.9 and 23.8 degrees 2-theta±0.2 degrees 2-theta and a XRPD pattern as depicted in FIG. 1.

Crystalline form N1 of Netarsudil mesylate is netarsudil:methanesulfonic acid 1:2.

Figure 2:
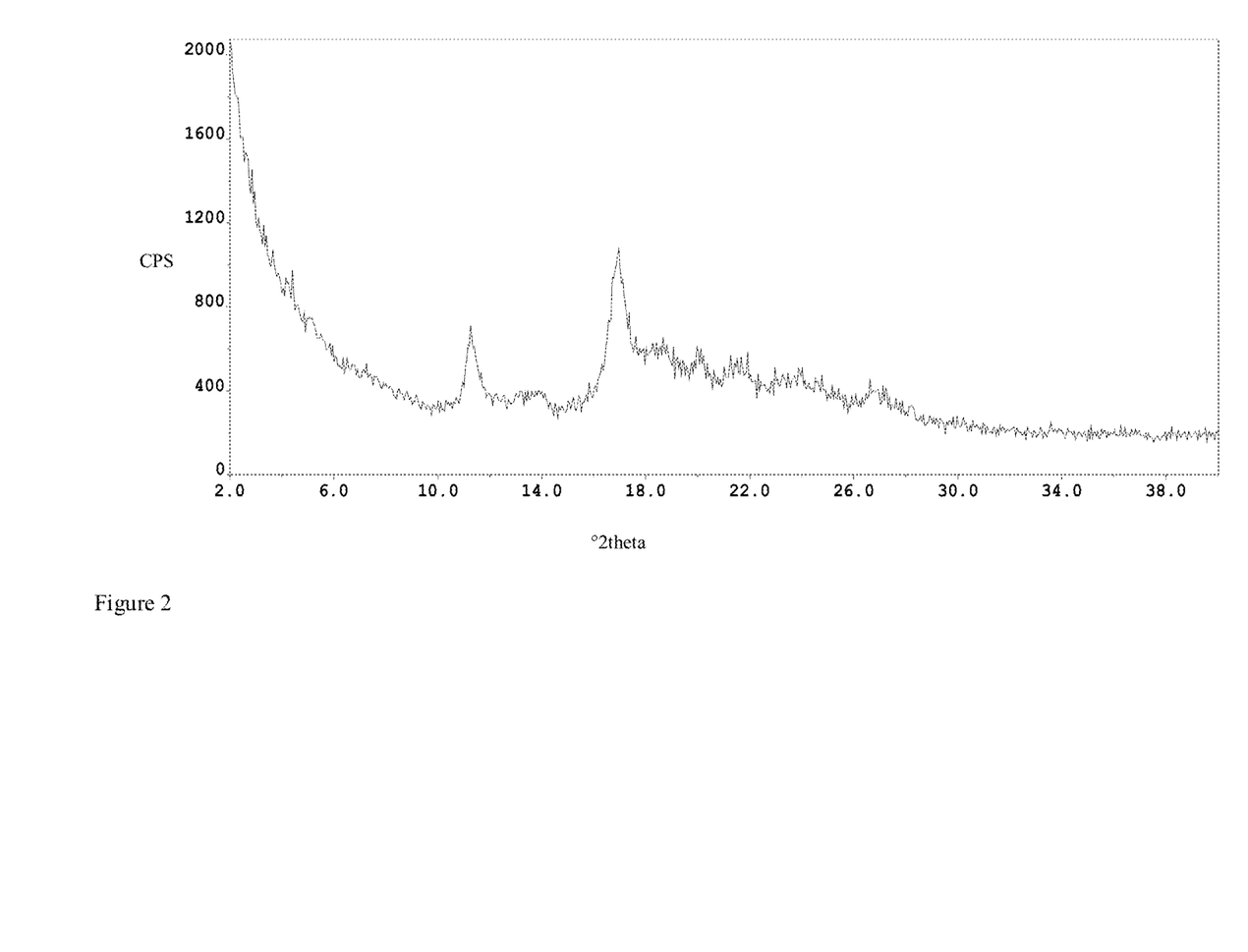
FIG. 2 shows a powder X-ray diffraction pattern of Netarsudil mesylate form N2 obtained in Example 2.

The present disclosure comprises a crystalline form of Netarsudil mesylate designated as form N2. The crystalline form N2 of Netarsudil mesylate can be characterized by data selected from one or more of the following: a XRPD pattern having peaks at 11.3 and 17.0 degrees 2-theta±0.2 degrees 2-theta; a XRPD pattern as depicted in FIG. 2; or combinations of these data.

Crystalline form N2 of Netarsudil mesylate is netarsudil:methanesulfonic acid 1:2, i.e. Netarsudil dimesylate.

Figure 3:
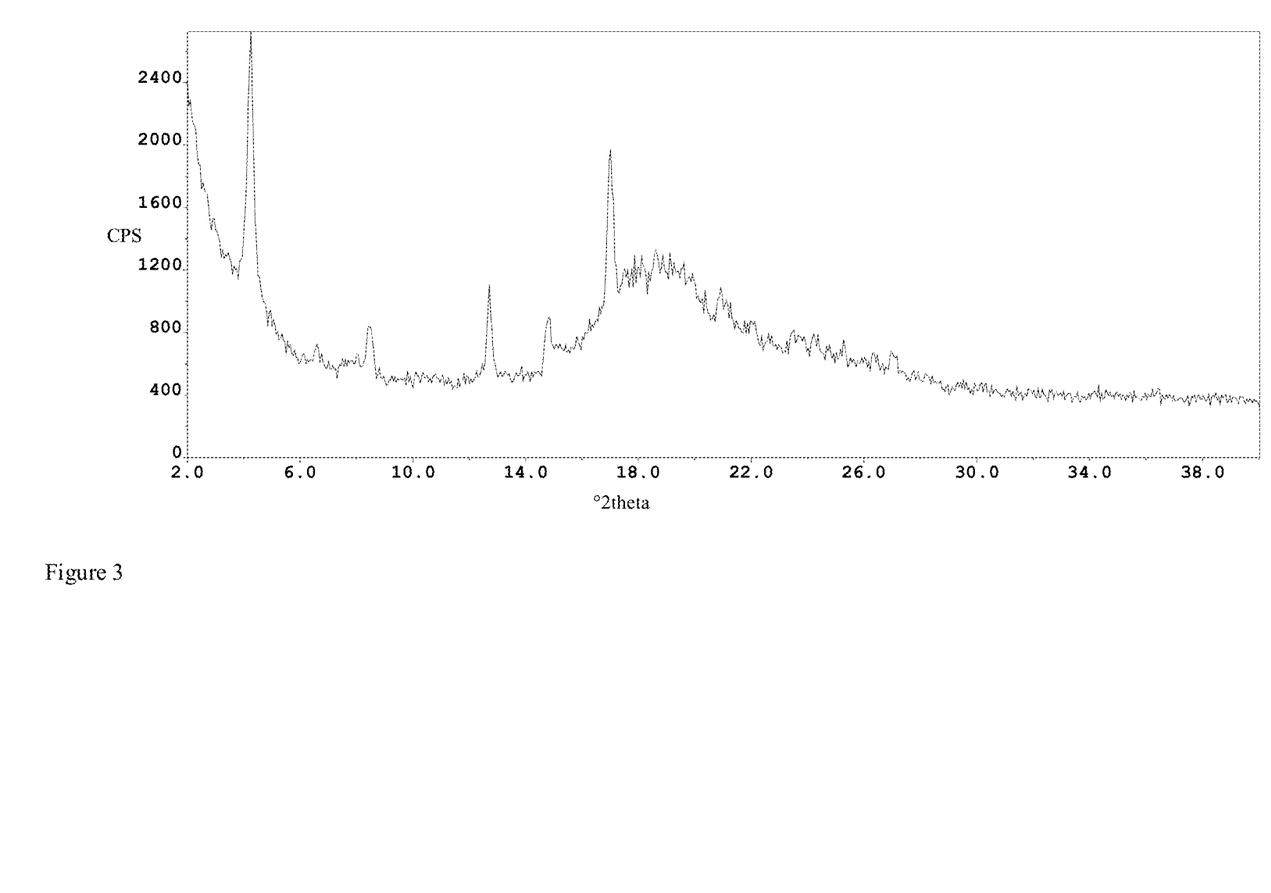
FIG. 3 shows a powder X-ray diffraction pattern of Netarsudil mesylate form N3 obtained in Example 3.

The present disclosure comprises a crystalline form of Netarsudil mesylate designated as form N3. The crystalline form N3 of Netarsudil mesylate can be characterized by data selected from one or more of the following: a XRPD pattern having peaks at 4.3, 8.5, 12.7, 14.8 and 17.0 degrees 2-theta±0.2 degrees 2-theta; a XRPD pattern as depicted in FIG. 3; or combinations of these data.

Crystalline form N3 of Netarsudil mesylate is netarsudil:methanesulfonic acid 1:2, i.e. Netarsudil dimesylate.

Figure 4:
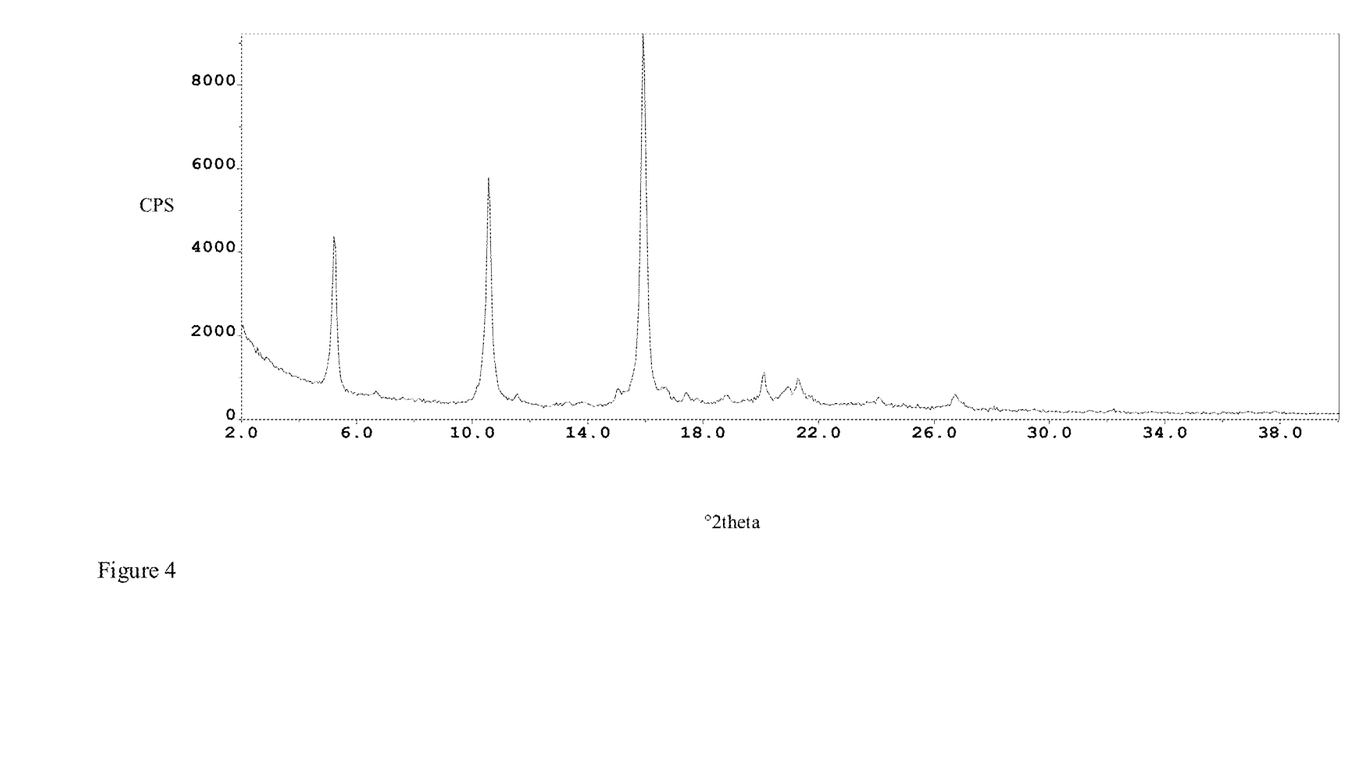
FIG. 4 shows a powder X-ray diffraction pattern of Netarsudil mesylate form N4 obtained in Example 6.

The present disclosure comprises a crystalline form of Netarsudil mesylate designated as form N4. The crystalline form N4 of Netarsudil mesylate can be characterized by data selected from one or more of the following: a XRPD pattern having peaks at 5.4, 10.7, and 16.1 degrees 2-theta±0.2 degrees 2-theta; a XRPD pattern as depicted in FIG. 4; or combinations of these data.

The present disclosure comprises a crystalline form of Netarsudil mesylate designated as form N5. The crystalline form N5 of Netarsudil mesylate can be characterized by data selected from one or more of the following: a XRPD pattern having peaks at 11.8, 13.2, 17.8, 18.9 and 20.2 degrees 2-theta±0.2 degrees 2-theta; a XRPD pattern as depicted in FIG. 5; or combinations of these data.

Crystalline form N5 of Netarsudil mesylate may be further characterized by the XRPD pattern having peaks at 11.8, 13.2, 17.8, 18.9 and 20.2 degrees 2-theta±0.2 degrees 2-theta, and also having one, two, three, four or five additional peaks at 13.6, 18.1, 21.7, 23.3 and 24.9 degrees 2-theta±0.2 degrees 2-theta; and combinations of these data.

Figure 5:
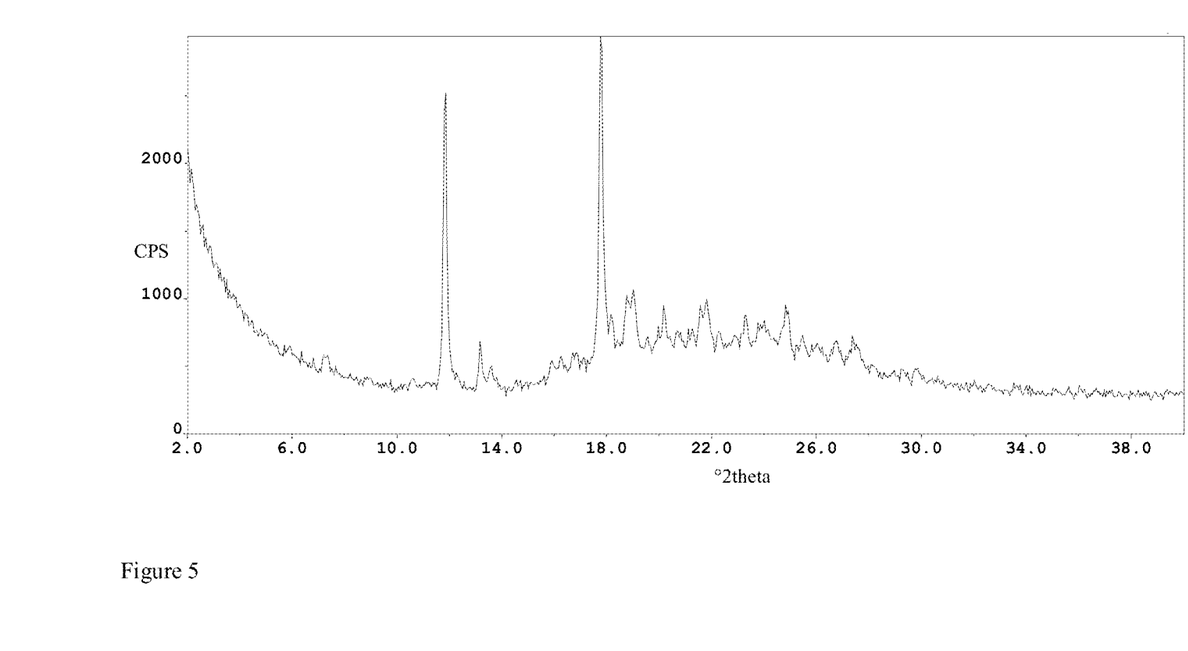
FIG. 5 shows a powder X-ray diffraction pattern of Netarsudil mesylate form N5 obtained in Example 7.

Crystalline form N5 of Netarsudil mesylate may be characterized by each of the above characteristics alone/or by all possible combinations, e.g., by XRPD pattern having peaks at 11.8, 13.2, 17.8, 18.9 and 20.2 degrees 2-theta±0.2 degrees 2-theta and a XRPD pattern as depicted in FIG. 5.

Crystalline form N5 of Netarsudil mesylate is netarsudil:methanesulfonic acid 1:2, i.e. Netarsudil dimesylate.

The present disclosure comprises a crystalline form of Netarsudil mesylate designated as form N6. The crystalline form N6 of Netarsudil mesylate can be characterized by data selected from one or more of the following: a XRPD pattern having peaks at 12.8, 14.3, 16.9, 18.6 and 20.4 degrees 2-theta±0.2 degrees 2-theta; a XRPD pattern as depicted in FIG. 6; or combinations of these data.

Crystalline form N6 of Netarsudil mesylate may be further characterized by the XRPD pattern having peaks at 12.8, 14.3, 16.9, 18.6 and 20.4 degrees 2-theta±0.2 degrees 2-theta, and also having one, two, three, four or five additional peaks at 15.7, 20.8, 23.0, 24.4 and 25.3 degrees 2-theta±0.2 degrees 2-theta; and combinations of these data.

Figure 6:
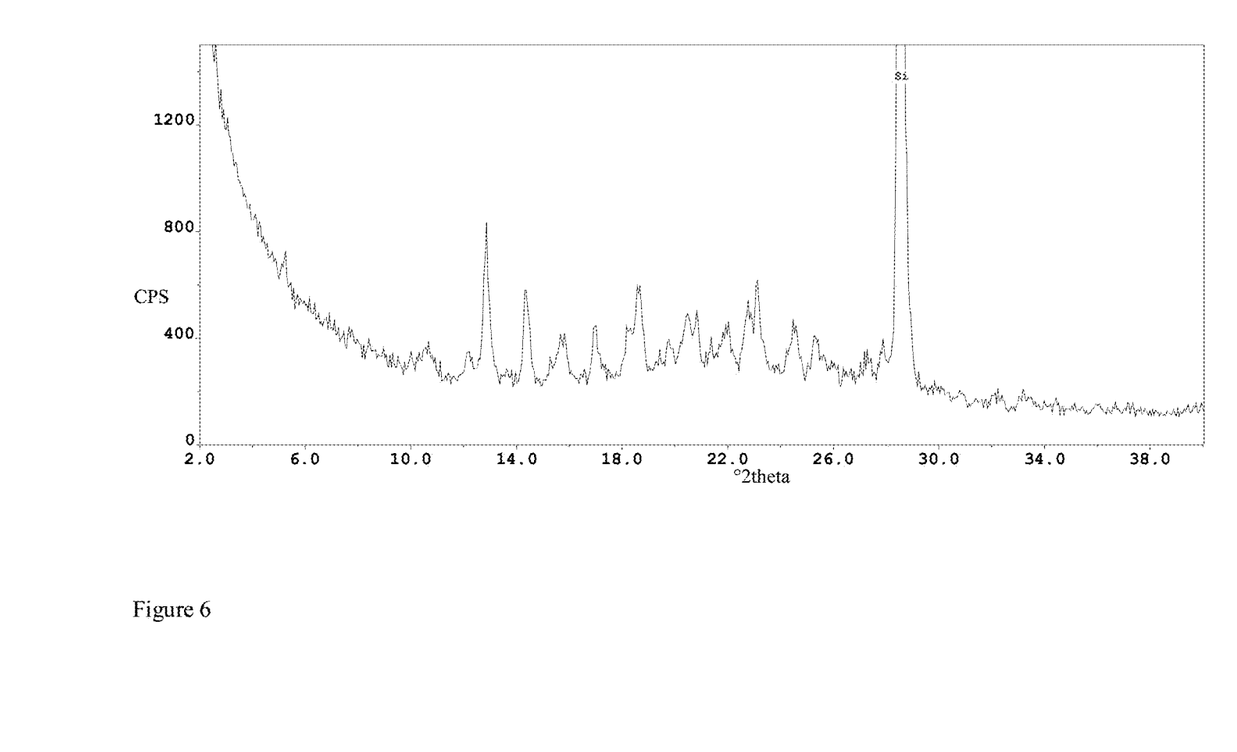
FIG. 6 shows a powder X-ray diffraction pattern of Netarsudil mesylate form N6 obtained in Example 8. The strong peak at about 28.5 degrees (marked with Si) is attributed to silicon powder added as an internal standard.

Crystalline form N6 of Netarsudil mesylate may be characterized by each of the above characteristics alone/or by all possible combinations, e.g., by XRPD pattern having peaks at 12.8, 14.3, 16.9, 18.6 and 20.4 degrees 2-theta±0.2 degrees 2-theta and a XRPD pattern as depicted in FIG. 6.

The present disclosure comprises a crystalline form of Netarsudil mesylate designated as form N7. The crystalline form N7 of Netarsudil mesylate can be characterized by data selected from one or more of the following: a XRPD pattern having peaks at 5.8, 11.5, 17.2, 19.0 and 21.5 degrees 2-theta±0.2 degrees 2-theta; a XRPD pattern as depicted in FIG. 7; or combinations of these data.

Crystalline form N7 of Netarsudil mesylate may be further characterized by the XRPD pattern having peaks at 5.8, 11.5, 17.2, 19.0 and 21.5 degrees 2-theta±0.2 degrees 2-theta, and also having one, two, three, four or five additional peaks at 13.9, 15.0, 16.5, 18.0 and 22.7 degrees 2-theta±0.2 degrees 2-theta; and combinations of these data.

Figure 7:
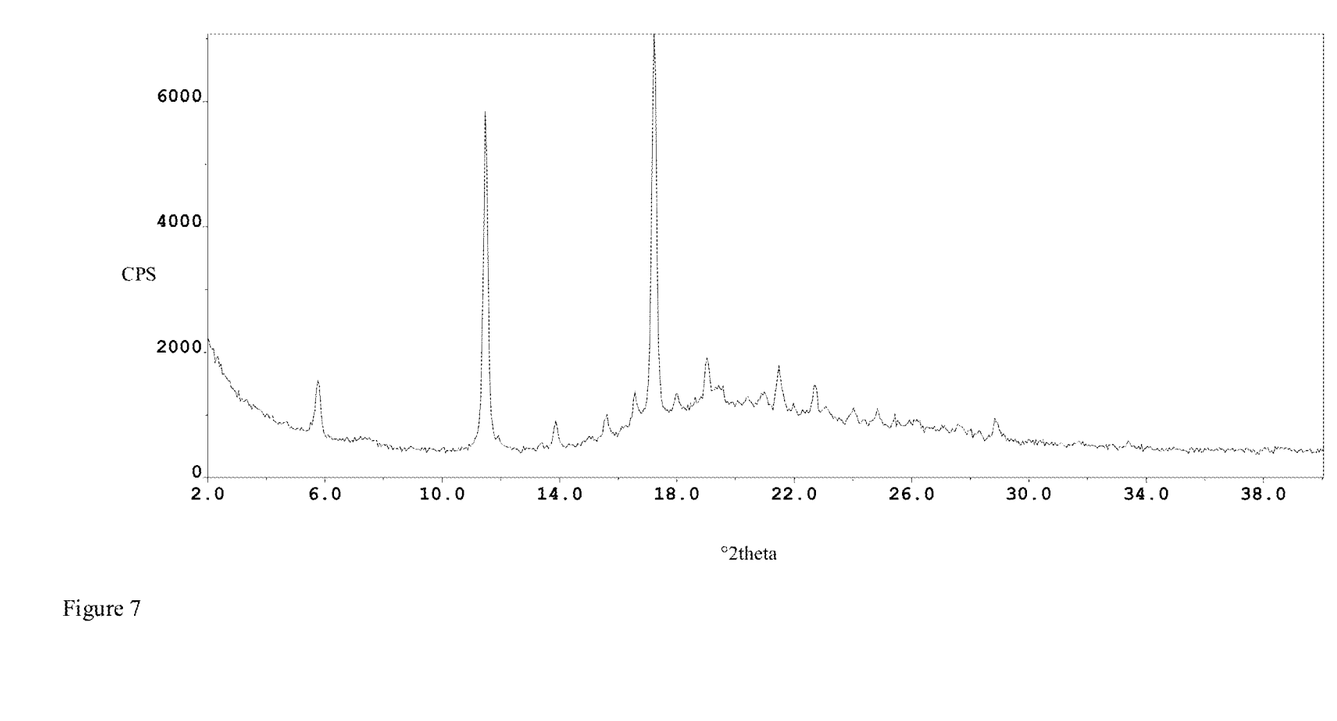
FIG. 7 shows a powder X-ray diffraction pattern of Netarsudil mesylate form N7 obtained in Example 9.

Crystalline form N7 of Netarsudil mesylate may be characterized by each of the above characteristics alone/or by all possible combinations, e.g., by XRPD pattern having peaks at 5.8, 11.5, 17.2, 19.0 and 21.5 degrees 2-theta±0.2 degrees 2-theta and a XRPD pattern as depicted in FIG. 7.

Crystalline form N7 of Netarsudil mesylate is netarsudil:methanesulfonic acid 1:2, i.e. Netarsudil dimesylate.

Crystalline form N7 is obtained as a white solid with high chemical purity with high factor purification of the (R)-isomer. Without wishing to be bound by any theory, netarsudil mesylate form N7 may comprise reduced amount of (R)-isomer by about 5-10 times compared to the starting material (S)-4-(3-((tert-butoxycarbonyl)amino)-1-(isoquinolin-6-ylamino)-1-oxopropan-2-yl)benzyl 2,4-dimethylbenzoate, therefore the amount (S)-isomer would be higher.

The present disclosure further encompasses processes for preparing Netarsudil salts or solid state forms thereof. The process comprises preparing the solid state form of the present disclosure, and converting it to other Netarsudil salt and solid state forms thereof or other solid state forms of the same salt. The conversion can be done, for example, by a process comprising reacting the obtained Netarsudil with an appropriate acid to obtain the corresponding acid addition salt.

The present disclosure further encompasses a pharmaceutical composition or formulation prepared by combining the solid state form of the present disclosure and at least one pharmaceutically acceptable excipient.

In another embodiment the present disclosure encompasses the above described solid state forms of Netarsudil and salts thereof, for use in the preparation of pharmaceutical compositions and/or formulations, preferably for the treatment of glaucoma or ocular hypertension.

In another embodiment the present disclosure encompasses the use of the above described solid state forms of Netarsudil and salts thereof, or combinations thereof, for the preparation of pharmaceutical compositions and/or formulations, preferably for local treatment in a form of ophthalmic solution.

The present disclosure further provides pharmaceutical compositions comprising the solid state forms of Netarsudil and salts thereof, or combinations thereof, according to the present disclosure.

In yet another embodiment, the present disclosure encompasses pharmaceutical formulations comprising at least one of the above described solid state forms of Netarsudil and salts thereof, and at least one pharmaceutically acceptable excipient.

The present disclosure encompasses a process to prepare said formulations of Netarsudil and salts thereof comprising combining at least one of the above solid state forms and at least one pharmaceutically acceptable excipient.

The solid state forms as defined herein, as well as the pharmaceutical compositions or formulations of Netarsudil and salts thereof can be used as medicaments, particularly for the treatment of glaucoma or ocular hypertension.

The present disclosure also provides a method of treating glaucoma or ocular hypertension, comprising administering a therapeutically effective amount of the solid state form of Netarsudil and salts thereof of the present disclosure, or at least one of the above pharmaceutical compositions or formulations, to a subject suffering from glaucoma or ocular hypertension or otherwise in need of the treatment.

The present disclosure also provides the use of the solid state forms of Netarsudil and salts thereof of the present disclosure, or at least one of the above pharmaceutical compositions or formulations for the manufacture of a medicament for glaucoma or ocular hypertension.

Having described the invention with reference to certain preferred embodiments, other embodiments will become apparent to one skilled in the art from consideration of the specification. The invention is further illustrated by reference to the following examples describing in detail the preparation of the composition and methods of use of the invention. It will be apparent to those skilled in the art that many modifications, both to materials and methods, may be practiced without departing from the scope of the invention.

Analytical Methods

X-Ray Powder Diffraction Method:

XRPD analysis was performed on ARL (SCINTAG) powder X-Ray diffractometer model X'TRA equipped with a solid state detector. Copper radiation of 1.5418 Å was used. Scanning parameters: range: 2-40 degrees two-theta; scan mode: continuous scan; step size: 0.05°, and a rate of 3 deg/min.

EXAMPLES

The starting materials Netarsudil base and (S)-4-(3-((tert-butoxycarbonyl)amino)-1-(isoquinolin-6-ylamino)-1-oxo-propan-2-yl)benzyl 2,4-dimethylbenzoate can be prepared according to the U.S. Pat. No. 8,394,826.

Example 1: Preparation of Netarsudil Mesylate Form N1

To a stirred solution of Netarsudil base (0.5 g, 1 eq) in isopropyl alcohol (IPA) (2.5 mL, 5 vol), methanesulfonic acid (166.88 µL, 2.15 eq) was added. After few minutes a precipitate was obtained and the slurry mixture was stirred for 2 days at RT. The solid was filtered under nitrogen, washed with IPA and dried in vacuum oven at 50° C. over the weekend to give Netarsudil mesylate form N1. Netarsudil mesylate form N1 has been confirmed by XRPD as presented in FIG. 1.

Netarsudil mesylate Form N1 is netarsudil:methanesulfonic acid 1:2 as confirmed by analytical techniques such as $^1$H-NMR and $^{13}$C-NMR.

Example 2: Preparation of Netarsudil Mesylate Form N2

To a solution of Netarsudil base (0.3 g, 1 eq) in 2-butanol (3.3 ml, 11 vol) under nitrogen atmosphere, a solution of methanesulfonic acid (100 µL, 2.15 eq) in diethyl ether (1 mL) was added dropwise using syringe pump (10 µL/min.) at 0° C. A precipitate was obtained and the slurry mixture was stirred for 2 days at 0° C. The solid was filtered under nitrogen, washed with 2-butanol and dried in vacuum oven at 50° C. over the weekend to give Netarsudil mesylate form N2. Netarsudil mesylate form N2 has been confirmed by XRPD as presented in FIG. 2.

Example 3: Preparation of Netarsudil Mesylate Form N3

Netarsudil mesylate Form N1 (50 mg) was placed in a plastic tube and inserted to a vial filled with 2 ml of BuOH (n-butanol). The vial was tightly closed for 1 week and after 1 week to give Netarsudil mesylate form N3. Netarsudil mesylate form N3 has been confirmed by XRPD as presented in FIG. 3.

Example 4: Preparation of Netarsudil Mesylate Form N4

Netarsudil mesylate Form N1 (50 mg) was placed in a plastic tube and inserted to a vial filled with 2 ml of ethanol. The vial was tightly closed for 1 week to give Netarsudil mesylate form N4. Netarsudil mesylate form N4 has been confirmed by XRPD.

Example 5: Preparation of Netarsudil Mesylate Form N4

Netarsudil mesylate Form N1 (50 mg) was placed in a plastic tube and inserted to a vial filled with 2 ml of toluene. The vial was tightly closed for 1 week and after 1 week to give Netarsudil mesylate form N4. Netarsudil mesylate form N4 has been confirmed by XRPD.

Example 6: Preparation of Netarsudil Mesylate Form N4

Netarsudil mesylate Form N1 (50 mg) was placed in a plastic tube and inserted to a vial filled with 2 ml of 1-PrOH (1-Propanol). The vial was tightly closed for 1 week to give Netarsudil mesylate form N4. Netarsudil mesylate form N4 has been confirmed by XRPD as presented in FIG. 4.

Example 7: Preparation of Netarsudil Mesylate Form N5

Netarsudil mesylate Form N1 (50 mg) was placed in a plastic tube and inserted to a vial filled with 2 ml of Acetonitrile. The vial was tightly closed for 1 week to give Netarsudil mesylate form N5. Netarsudil mesylate form N5 has been confirmed by XRPD as presented in FIG. 5.

Example 8: Preparation of Netarsudil Mesylate Form N6

Netarsudil free base (1 eq) and 2-BuOH (11 vol) were charged in 250 ml reactor and the mixture was stirred under nitrogen atmosphere at RT to give an oily suspension. The reactor content was cooled to 0° C. and a solution of MSA (methanesulfonic acid) (2.15 eq) in diethyl ether (3.75 vol) was added dropwise by a syringe pump (10 µL/min) under nitrogen atmosphere at 0° C. during 20 hr. A precipitate was obtained and the slurry mixture was stirred for 1 day at 0° C. The solid was filtered under nitrogen, washed with 2-BuOH and dried in vacuum oven at 50° C. for 72 hr to give Netarsudil mesylate form N6. Netarsudil mesylate form N6 has been confirmed by XRPD as presented in FIG. 6.

Example 9: Preparation of Netarsudil Mesylate Form N7

Netarsudil mesylate Form N1 (50 mg) was placed in a plastic tube and inserted to a vial filled with 2 ml of iso-butanol. The vial was tightly closed for 1 week to give Netarsudil mesylate form N7. Netarsudil mesylate form N7 has been confirmed by XRPD as presented in FIG. 7.

Example 10: Preparation of Netarsudil Mesylate Form N3

To a stirred solution of (S)-4-(3-((tert-butoxycarbonyl) amino)-1-(isoquinolin-6-ylamino)-1-oxopropan-2-yl)benzyl 2,4-dimethylbenzoate (5.0 g 1 eq.) in DCM (dichloromethane) (10 vol), methanesulfonic acid (2.5 eq) was added dropwise. The reaction mixture was stirred at room temperature over 15 h and completion of the reaction was ascertained by HPLC. A gradual solvent switch from DCM to 2-BuOH was then carried out. The solution of the DCM solvent was removed by distillation under vacuum. Next, two substantial portions of 2-BuOH were added to the residue follows by vacuum distillation. Eventually, 2-BuOH (10 vol) was added to the residue and the reaction mixture was stirred at room temperature over a period of 15 h.

The dimesylate salt was isolated as a solid by filtration under nitrogen. After washing with 2-BuOH (2×1 vol) and heptane (2×1 vol), the solid was dried upon vacuum oven at 40° C. over 15 h. The compound was obtained as a white solid (2.52 g). Netarsudil mesylate form N3 has been confirmed by XRPD.

Example 11: Preparation of Netarsudil Mesylate Form N7

To a stirred solution of (S)-4-(3-((tert-butoxycarbonyl) amino)-1-(isoquinolin-6-ylamino)-1-oxopropan-2-yl)benzyl 2,4-dimethylbenzoate (5.0 g 1 eq.) in DCM (dichloromethane) (10 vol), methanesulfonic acid (2.5 eq) was added dropwise. The reaction mixture was stirred at room temperature over 4 h and completion of the reaction was ascertained by HPLC. A gradual solvent switch from dichloromethane to 2-BuOH was then carried out. The solution of the DCM solvent was removed by distillation under vacuum. Next, two substantial portions of 2-BuOH were added to the residue follows by vacuum distillation. Eventually, 2-BuOH (10 vol) was added to the residue and the reaction mixture was stirred at room temperature over a period of 15 h.

The dimesylate salt was isolated as a solid by filtration under nitrogen. After washing with 2-BuOH (2×1 vol) and heptane (2×1 vol), the solid was dried upon vacuum oven at 50° C. over 15 h. The compound was obtained as a white solid (4.81 g, 99.9% purity and contained 0.10% (R)-isomer). Netarsudil mesylate form N7 has been confirmed by XRPD.

The invention claimed is:

1. Crystalline form N1 of Netarsudil mesylate characterized by data selected from one or more of the following:
    (i) a PXRD pattern having peaks at 5.8, 11.9, 17.8, 19.9 and 23.8 degrees 2-theta±0.2 degrees 2-theta;
    (ii) a PXRD pattern as depicted in FIG. 1;
    (iii) a PXRD pattern having peaks at 5.8, 11.9, 17.8, 19.9 and 23.8 degrees 2-theta±0.2 degrees 2-theta, and also having one, two, three or four additional peaks at 6.8, 21.2, 24.5 and 26.6 degrees 2-theta±0.2 degrees 2-theta; and
    (iv) combinations of any of (i)-(iii).

2. A pharmaceutical composition or formulation comprising crystalline form N1 of Netarsudil mesylate according to claim 1 and at least one pharmaceutically acceptable excipient.

3. A pharmaceutical composition or formulation prepared by combining the crystalline form N1 of Netarsudil mesylate according to claim 1 and at least one pharmaceutically acceptable excipient.

4. The pharmaceutical composition or formulation according to claim 2 for local treatment in a form of an ophthalmic solution.

5. A process for preparing a pharmaceutical composition or formulation according to claim 2 comprising combining the crystalline form N1 of Netarsudil mesylate and at least one pharmaceutically acceptable excipient.

6. A process for preparing a pharmaceutical composition or formulation of Netarsudil and salts thereof comprising converting the crystalline form N1 of Netarsudil mesylate according to claim 1 to Netarsudil or salt thereof; and combining Netarsudil or salt thereof with at least one pharmaceutically acceptable excipient.

7. A method of treating glaucoma or ocular hypertension, comprising administering a therapeutic effective amount of crystalline form N1 of Netarsudil mesylate according to claim 1 to a subject suffering from glaucoma or ocular hypertension.

8. A method of treating glaucoma or ocular hypertension, comprising administering the pharmaceutical composition or formulation according to claim 2 to a subject suffering from glaucoma or ocular hypertension.

9. A method of treating glaucoma or ocular hypertension, comprising administering the pharmaceutical composition or formulation according to claim 3 to a subject suffering from glaucoma or ocular hypertension.

* * * * *